United States Patent
Hong et al.

(10) Patent No.: US 12,005,142 B2
(45) Date of Patent: Jun. 11, 2024

(54) SUSTAINED-RELEASE COMPOSITIONS COMPRISING A THERAPEUTIC AGENT FOR TREATING DEPRESSION OR ANXIETY AND USES THEREOF

(71) Applicants: TAIWAN LIPOSOME CO., LTD., Taipei (TW); TLC BIOPHARMACEUTICALS, INC., South San Francisco, CA (US)

(72) Inventors: Keelung Hong, South San Francisco, CA (US); Yi-Yu Lin, South San Francisco, CA (US); Hao-Wen Kao, South San Francisco, CA (US)

(*) Notice: Subject to any disclaimer, the term of this patent is extended or adjusted under 35 U.S.C. 154(b) by 213 days.

(21) Appl. No.: 17/264,552

(22) PCT Filed: Jul. 31, 2019

(86) PCT No.: PCT/US2019/044309
§ 371 (c)(1),
(2) Date: Jan. 29, 2021

(87) PCT Pub. No.: WO2020/028475
PCT Pub. Date: Feb. 6, 2020

(65) Prior Publication Data
US 2021/0308052 A1   Oct. 7, 2021

Related U.S. Application Data

(60) Provisional application No. 62/775,124, filed on Dec. 4, 2018, provisional application No. 62/713,895, filed on Aug. 2, 2018.

(51) Int. Cl.
*A61K 9/127* (2006.01)
*A61K 9/00* (2006.01)
(Continued)

(52) U.S. Cl.
CPC ......... *A61K 9/1273* (2013.01); *A61K 9/0019* (2013.01); *A61K 31/135* (2013.01);
(Continued)

(58) Field of Classification Search
CPC .... A61K 9/127; A61K 9/1278; A61K 9/1273; A61K 9/0019; A61K 31/135;
(Continued)

(56) References Cited

U.S. PATENT DOCUMENTS 9,877,918 B2 * 1/2018 Yamashita ........... A61K 9/1277
2007/0275048 A1 * 11/2007 Liu ...................... A61K 31/724
514/184
(Continued)

FOREIGN PATENT DOCUMENTS

CN       101601654 A    12/2009
CN       102406606 B    1/2013
(Continued)

OTHER PUBLICATIONS

Office Action for related China Application No. 201980051355.4, dated Jun. 29, 2022.
(Continued)

*Primary Examiner* — Gollamudi S Kishore
(74) *Attorney, Agent, or Firm* — Piloff Passino & Cosenza LLP; Rachel K. Piloff; Sean A. Passino (57) ABSTRACT

The present invention relates to a pharmaceutical composition comprising at least one liposome and a therapeutic agent for treating depression or anxiety, with a therapeutic agent to lipid ratio equal to or higher than about 0.15. The pharmaceutical composition improves the pharmacokinetic
(Continued)

profile and sustains the release of the therapeutic agent. Also provided is the method for treating depression or anxiety using the pharmaceutical composition disclosed herein.

20 Claims, 2 Drawing Sheets

(51) Int. Cl.
  *A61K 31/135* (2006.01)
  *A61K 31/439* (2006.01)
  *A61K 47/24* (2006.01)
  *A61K 47/26* (2006.01)
  *A61K 47/28* (2006.01)
(52) U.S. Cl.
  CPC ............ *A61K 31/439* (2013.01); *A61K 47/24* (2013.01); *A61K 47/26* (2013.01); *A61K 47/28* (2013.01)
(58) Field of Classification Search
  CPC ...... A61K 31/439; A61K 47/24; A61K 47/26; A61K 47/28; A61K 47/02; A61K 31/46; A61K 9/1271; A61P 25/28; A61P 25/00; A61P 25/24; A61P 25/22
  See application file for complete search history.

(56) References Cited

U.S. PATENT DOCUMENTS

| | | | |
|---|---|---|---|
| 2008/0031935 A1* | 2/2008 | Bodenteich | A61K 9/127 514/297 |
| 2008/0095831 A1 | 4/2008 | McGraw | |
| 2013/0202686 A1 | 8/2013 | Yamashita et al. | |
| 2014/0220110 A1 | 8/2014 | Hayes et al. | |
| 2017/0042878 A1* | 2/2017 | Fava | A61K 31/46 |
| 2017/0266295 A1* | 9/2017 | Kan | A61K 31/704 |
| 2017/0340624 A1 | 11/2017 | Hong et al. | |
| 2021/0378961 A1 | 12/2021 | Hong et al. | |

FOREIGN PATENT DOCUMENTS

| | | |
|---|---|---|
| CN | 105163720 A | 12/2015 |
| CN | 107260680 A | 10/2017 |
| CN | 112512508 A | 3/2021 |
| WO | 2014121211 A2 | 8/2014 |
| WO | 2014121235 A2 | 8/2014 |
| WO | 2020023445 A1 | 1/2020 |

OTHER PUBLICATIONS

Jun Chen et al., "Preparation and pharmacokinetic investigation of propranolol-loaded elastic liposomes composed of DP-PC and SPC," Chinese Pharmaceutical Journal, Oct. 22, 2013, pp. 1,761-1,765, vol. 48, No. 20.
Zhen-Zhen Yang et al., "Enhanced brain distribution and pharmacodynamics of rivastigmine by liposomes following intranasal administration," International Journal of Pharmaceutics, May 13, 2013, pp. 344-354, vol. 452, No. 1.
Serge A Steenen et al., "Propranolol for the treatment of anxiety disorders: Systematic review and meta-analysis", Journal of Psychopharmacology., Feb. 1, 2016, pp. 128-139, vol. 30, No. 2.
Dawn F. Ionescu et al., "Ziprasidone augmentation for anxious depression*", International Clinical Psychopharmacology, Nov. 1, 2016, pp. 341-346, vol. 31, No. 6.
Anonymous: "Cerenia for Pets 101: Understanding Side Effects—Innovet Pet" Dec. 20, 2018 Retrieved from Internet: URL:https://www.innovetpet.com/blogs/medications/cerenia-for-dogs [retrieved on Mar. 23, 2022].
Luciano Roman-Albasini et al., "Antidepressant-relevant behavioral and synaptic molecular effects of long-term fasudil treatment in chronically stressed male rats," Neurobiology of Stress, Nov. 1, 2020, pp. 10,0234-10,0234, No. 13.
Narong Maneeton et al., "Quetiapine monotherapy in acute treatment of generalized anxiety disorder: a systematic review and meta-analysis of randomized controlled trials," Drug Design, Development and Therapy, Jan. 1, 2016, pp. 259-276, vol. 10.
Kannayiram Alagiakrishnan, "Galantamine in the Treatment of Minor Depression With Mild to Moderate Alzheimer's Dementia in an Elderly Woman," The Primary Care Companion to the Journal of Clinical Psychiatry: The Official Journal of the Association of Medicine and Psychiatry, Jan. 1, 2010, vol. 12, No. 3.
Paul J. Fitzgerald et al., "The cholinesterase inhibitor donepezil has antidepressant-like properties in the mouse forced swim test," Translational Psychiatry, Dec. 1, 2020, vol. 10, No. 1.
Office Action for related Europe Application No. 19843786.5, dated Apr. 5, 2022.
Sara Nageeb El-Helaly et al., "Electrosteric stealth Rivastigmine loaded liposomes for brain targeting: preparation, characterization, ex vivo, bio-distribution and in vivo pharmacokinetic studies," Drug Delivery, Apr. 18, 2017, pp. 692-700, vol. 24, No. 1.
International Search Report & Written Opinion for PCT/US2019/044309, dated Oct. 2, 2019.
Office Action for related Taiwan application, dated May 15, 2020.
Office Action for related Taiwan application, dated Aug. 11, 2020.

* cited by examiner

SUSTAINED-RELEASE COMPOSITIONS COMPRISING A THERAPEUTIC AGENT FOR TREATING DEPRESSION OR ANXIETY AND USES THEREOF

CROSS-REFERENCE TO RELATED APPLICATIONS

This application claims the benefit of U.S. Application No. 62/713,895 filed on 2 Aug. 2018 and U.S. Application No. 62/775,124, filed on 4 Dec. 2018, the entire disclosures of which are incorporated herein by reference.

TECHNICAL FIELD

The present invention is directed to a sustained-release liposomal composition comprising a therapeutic agent for treating depression or anxiety with a high therapeutic agent to lipid ratio using at least one trapping agent. The high therapeutic agent to lipid ratio and sustained release profile of the liposomal composition reduce the frequency of drug administration, increase patient compliance and improve the therapeutic outcome.

BACKGROUND

Liposomes as a drug delivery system is a successful technology and has been widely used for developing sustained-release formulations for various drugs. Drug loading into liposomes can be attained either remotely/actively (creating a transmembrane pH- or ion-gradient during liposome formation, followed by loading the drug by the driving force generated from the gradient after liposome formation) or passively (the drug is encapsulated during liposome formation), see U.S. Pat. Nos. 5,192,549 and 5,939,096. Although methods of drug loading into liposomes are well documented in the literature, only a handful of therapeutic agents were successfully loaded into liposomes with high encapsulation efficiencies. Various factors can affect the drug encapsulation efficiency, including but not limited to, physical and chemical properties of the therapeutic agent, for example, hydrophilic/hydrophobic characteristics, dissociation constant, solubility and partition coefficient, lipid composition, trapping agent, reaction solvent, and particle size (Proc Natl Acad Sci USA. 2014; 111(6): 2283-2288 and Drug Metab Dispos. 2015; 43 (8): 1236-45).

Glutamate N-methyl-D-aspartate (NMDA) receptor antagonist, such as ketamine, has been used to treat depression and anxiety. Its antidepressant response is observed within hours of a single intravenous infusion to rapidly reduce suicidal ideation in depressed patients. A randomized trial of treatment-resistant depression patents reported that 71% of the 17 patients showed a >50% decrease in Hamilton Depression Rating Scale (HDRS) score one day after a single intravenous infusion of ketamine and the therapeutic response was maintained for a week in 35% of the patients (Arcg Gen Psychiatry. 2006; 63(8):856-64). To maintain the antidepressant effect and avoid relapse, a repeated intravenous infusion study (three infusions per week) in treatment-resistant depression patients showed that eight of nine subjects relapsed within 19 days after the final intravenous infusion (Biol Psychiatry. 2010; 67(2): 139-45). Even though the depression-free period was extended by the repeated intravenous doses, drawbacks of intravenous injection include a higher incidence of adverse side effects, regular hospital visits, and a higher cost for drug administration due to the infusion equipment and the requirement of trained staff to administer the drug, all of which limit the use of ketamine infusion. Oral administration of ketamine for treating depression has been reported by Al Shirawi et al. (J Clin Psychopharmacol. 2017; 37(4):464-467) but only approximately 30% of patients showed improvement of mood symptoms as oral bioavailability of ketamine is only 17% (Br J Anaesth. 1981; 53(8):805-10).

Scopolamine, a muscarinic cholinergic antagonist, significantly improves the symptoms of depression within a few days of an intravenous injection (Arch Gen Psychiatry. 2006; 63:1121-1129). Of the eight patients enrolled in the study, five patients demonstrated a 50% or greater reduction in Montgomery-Asberg Depression Rating Scale (MADRS) scores, and 3 remitted to the nondepressed range (MADRS score 10). To maintain the antidepressant effect, repeated intravenous infusions of scopolamine were administered to subjects with major depressive disorder (n=18, a total of 3 infusions with a 3-5 days interval between the infusions) in a double-blind, placebo-controlled, crossover clinical trial (Biol Psychiatry 2010; 67:432-438). Although clinical improvement persisted for more than 2 weeks following the final scopolamine infusion, drawbacks of intravenous infusions include a higher incidence of dose dependent adverse side effects (hallucination, vertigo, dry mouth and drowsiness), regular hospital visits, and a higher cost due to equipment and staffing, all of which limit the use of scopolamine infusion.

There is an unmet need to optimize the balance between maintaining the plasma concentration of a therapeutic agent for treating depression or anxiety and the safety/tolerance of these therapeutic agents. The present invention addresses this need and other needs.

SUMMARY OF THE INVENTION

In one embodiment, a sustained release pharmaceutical composition comprises (a) at least one liposome comprising a bilayer membrane, said bilayer membrane comprises at least one lipid; (b) a trapping agent; and (c) a therapeutic agent for treating depression or anxiety, wherein the molar ratio of the therapeutic agent to the lipid is equal to or higher than about 0.15 is provided.

According to another embodiment of the present invention, methods are provided for treating depression and/or anxiety, comprising the steps of administering a pharmaceutical composition described herein to a subject in need thereof.

Also provided are the use of the pharmaceutical composition described herein in the manufacture of a medicament for therapeutic and/or prophylactic treatment of depression and/or anxiety disorder.

Further provided is a medicament for treating depression and/or anxiety, comprising a therapeutically effective amount of the pharmaceutical composition described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

A further understanding of the nature and advantages of the present invention may be realized by reference to the remaining portions of the specification and the drawings.

DETAILED DESCRIPTION OF THE INVENTION

As employed above and throughout the disclosure, the following terms, unless otherwise herein, the singular forms "a," "an" and "the" include the plural reference unless the context clearly indicates otherwise.

All numbers herein may be understood as modified by "about." As used herein, the term "about" refers to a range of ±10% of a specified value.

An "effective amount," as used herein, refers to the dose of a pharmaceutical composition to reduce or control the symptoms and signs of depression or anxiety, such as persistent sad or anxious mood, feelings of hopelessness, pessimism, nervousness and/or worthlessness, suicidal ideation or attempts, irritability, restlessness, difficulty concentrating, overeating, appetite loss, or insomnia. The term "effective amount" and "therapeutically effective amount" are used interchangeably.

The term "treating," "treated," or "treatment," as used herein, includes preventative (e.g. prophylactic), palliative, and curative methods, uses or results. The terms "treatment" or "treatments" can also refer to compositions or medicaments. Throughout this application, by treating is meant a method of reducing or delaying one or more symptoms or signs of depression and/or anxiety or the complete amelioration of depression or anxiety as detected by art-known techniques. Art recognized methods are available to evaluate depression or anxiety and its symptoms. These include, but are not limited to, psychiatric evaluation (such as DSM-5 diagnostic criteria), lab tests, imaging or assay of biomarkers (for example, measuring the level of neurotransmitters, measuring the ratio of glutamine to glutamate and measuring the density of GABA neurons), and imaging of neurobiological abnormalities. For example, a disclosed method is considered to be a treatment if there is at least 1% reduction in one or more symptoms of depression or anxiety in a subject when compared to the subject prior to treatment or control subjects. Thus, the reduction can be about a 1, 5, 10, 20, 30, 40, 50, 60, 70, 80, 90, 100%, or any amount of reduction in between.

The term "depression," as used herein, encompasses a variety of types and subtypes of various etiologies and causes, either known or unknown, including, but not limited to, major depressive disorder, bipolar disorder, treatment-resistant depression.

The term "anxiety," as used herein, encompasses a variety of types and subtypes of various etiologies and causes, either known or unknown, including, but not limited to, generalized anxiety disorder, panic disorder and social anxiety disorder.

The term "subject" can refer to a vertebrate having or at risk of developing depression or anxiety or to a vertebrate deemed to be in need of depression and/or anxiety treatment. Subjects include all warm-blooded animals, such as mammals, such as a primate, and, more preferably, a human. Non-human primates are subjects as well. The term "subject" includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Liposome

The terms "liposome," "liposomal" and related terms as used herein are characterized by an interior aqueous space sequestered from an outer medium by one or more bilayer membranes forming a vesicle. Non-limiting examples of liposomes include small unilamellar vesicles (SUV), large unilamellar vesicles (LUV), and multi-lamellar vesicles (MLU) with an average diameter ranges from 50 nm to 20 μm, 50 nm to 10 μm, 50 nm to 1000 nm, 50 nm to 500 nm, 50 nm to 400 nm, 50 nm to 300 nm, 50 nm to 250 nm, or 50 nm to 200 nm.

Bilayer membranes of liposomes are typically formed by at least one lipid, i.e. amphiphilic molecules of synthetic or natural origin that comprise spatially separated hydrophobic and hydrophilic domains. Examples of lipid, including but not limited to, dialiphatic chain lipids, such as phospholipids, diglycerides, dialiphatic glycolipids, single lipids such as sphingomyelin and glycosphingolipid, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-ra-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanolamine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanolamine (PEG-DS PE), 1,2-dioleoyl-sn-glycero-3-phosphoethanolamine (DOPE), 1,2-dipalmitoyl-sn-glycero-3-phospho-(1'-myo-inositol) (ammonium salt)

(DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). In some embodiments, the lipid is a lipid mixture of one or more of the foregoing lipids, or mixtures of one or more of the foregoing lipids with one or more other lipids not listed above, membrane stabilizers or antioxidants.

In some embodiments, the mole percent of the lipid in the bilayer membrane is equal or less than about 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40 or any value or range of values therebetween (e.g., about 40-80, about 40-75, about 40-70, about 40-65, about 45-80, about 45-75, about 45-70, about 45-65, about 50-80, about 50-75, about 50-70 or about 50-65).

In some embodiments, the lipid of the bilayer membrane comprises a mixture of a first lipid and a second lipid. In some embodiments, the first lipid is selected from the group consisting essentially of phosphatidylcholine (PC), HSPC, DSPC, DPPC, DMPC, PSPC and a combination thereof and the second lipid is selected from the group consisting essentially of a phosphatidylethanolamine, phosphatidylglycerol, PEG-DSPE, DPPG and a combination thereof. In other embodiments, the mole percent of the first lipid in the bilayer membrane is equal or less than about 79.9, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35 or any value or range of values therebetween (e.g., about 40-75%, about 40-70%, about 40-65%, about 45-75%, about 45-70%, about 45-65%, about 50-75%, about 50-70% or about 50-75% if the therapeutic agent is a NMDA receptor antagonist and about 35-79.9%, 35-75%, about 35-70%, about 35-65%, 40-75%, about 40-70%, about 40-65%, about 45-75%, about 45-70%, about 45-65%, if the therapeutic agent is a muscarinic cholinergic antagonist). The mole percent of the second lipid in the bilayer membrane is equal to or less than about 25, 24, 23, 22, 21, 20, 19, 18, 17, 16, 15, 14, 13, 12, 11, 10, 9, 8, 7, 6, 5, 4, 3, 2, 1, 0.1 or any value or range of values therebetween (e.g., about 0.1-25%, about 0.1-20%, about 0.5-25%, about 0.5-20% if the therapeutic agent is a muscarinic cholinergic antagonist and about 0.1-15%, about 0.1-10%, about 0.5-10%, about 0.5-10% if the therapeutic agent is a NMDA receptor antagonist).

Bilayer membranes of liposomes further comprise less than about 60 mole percentage of steroids, preferably cholesterol. In certain embodiments, the % of cholesterol in the bilayer membrane is about 20-60, about 20-55%, about 20-50, about 20-45%, about 20-40%, about 25-60, about 25-55%, about 25-50%, about 25-45%, about 25-40%, about 30-60%, about 30-55%, about 30-50%, about 30-45% or about 30-40%.

In one exemplary embodiment, the mole % of the lipid and cholesterol in the bilayer membrane is about 40-80%: 20-60% or 45-75%: 25-55%. In another exemplary embodiment, the mole % of the first lipid, the second lipid and cholesterol in the bilayer membrane is about 35-79.9%: 0.1%-25%: 20-60%, 35-75%: 0.1-25%: 20-50% or 40-70%: 0.1-25%: 25-45%.

Remote Loading

The term "remote loading" as used herein is a drug loading method which involves a procedure to transfer drugs from the external medium across the bilayer membrane of the liposome to the interior aqueous space by a polyatomic ion-gradient. Such gradient is generated by encapsulating at least one polyatomic ion as a trapping agent in the interior aqueous space of the liposome and replacing the outer medium of the liposome with an external medium with a lower polyatomic ion concentration, for example, pure water, sucrose solution and saline, by known techniques, such as column separation, dialysis, centrifugation or tangential flow filtration. A polyatomic ion gradient is created between the interior aqueous space and the external medium of the liposomes to trap the therapeutic agent in the interior aqueous space of the liposomes. Exemplary polyatomic ion as trapping agents include, but are not limited to, sulfate, sulfite, phosphate, hydrogen phosphate, molybdate, carbonate and nitrate. Exemplary trapping agents include, but are not limited to, ammonium sulfate, ammonium phosphate, ammonium molybdate, ammonium sucrose octasulfate, triethylammonium sucrose octasulfate and dextran sulfate.

In an embodiment, the concentration of triethylammonium sucrose octasulfate is about 10 to about 200 mM or about 50 to about 150 mM. In another embodiment, the concentration of ammonium sulfate is about 100 to about 600 mM, about 150 to about 500 mM or about 200 to about 400 mM. In yet another embodiment, the concentration of ammonium phosphate is about 100 to about 600 mM, about 150 to about 500 mM or about 200 to about 400 mM. In accordance with the invention, the liposome encapsulating a trapping agent can be prepared by any of the techniques now known or subsequently developed. For example, the MLV liposomes can be directly formed by a hydrated lipid film, spray-dried powder or lyophilized cake of selected lipid compositions with trapping agent; the SUV liposomes and LUV liposomes can be sized from MLV liposomes by sonication, homogenization, microfluidization or extrusion.

In some embodiments, the trapping agent is triethylammonium sucrose octasulfate, ammonium sulfate or a combination thereof if the therapeutic agent is an NMDA receptor antagonist. In some embodiments, the trapping agent is ammonium sulfate triethylammonium sucrose octasulfate, ammonium phosphate or a combination thereof if the therapeutic agent is a muscarinic cholinergic antagonist.

Pharmaceutical Compositions

The present invention is directed to a sustained release pharmaceutical composition, comprising (a) at least one liposome comprising a bilayer membrane, said bilayer membrane comprises at least one lipid; (b) a trapping agent; and (c) a therapeutic agent for treating depression or anxiety, wherein the molar ratio of the therapeutic agent to the lipid is above or equal to about 0.15. In some embodiment, the molar ratio of the therapeutic agent to the lipid is above or equal to 0.15 to less than about 10, less than about 5, less about 3, less than about 2, less than about 1, less than about 0.5.

In one embodiment, the sustained release pharmaceutical composition further comprises at least one pharmaceutically acceptable excipient, diluent, medium for the active ingredient, a preservative, cryoprotectant or a combination thereof. In one exemplary embodiment, the weight percentage of the therapeutic agent is about 0.02-2%, the weight percent of the bilayer membrane in the pharmaceutical composition is about 0.1-15%; the weight percent of the trapping agent in the pharmaceutical composition is about 0.1-20%; and the weight percent of the pharmaceutically acceptable excipient (such as sucrose, histidine, sodium chloride and ultrapure water), diluent, medium for the active ingredient, a preservative, cryoprotectant or a combination thereof in the pharmaceutical composition is about 65.0-99.9%.

In certain embodiments, the therapeutic agent for treating depression and anxiety is an NMDA receptor antagonist.

Non limiting examples of NMDA receptor antagonist include ketamine, norketamine, fourphit, memantine, rislenemdaz, traxoprodil, rapastinel and a combination thereof. The ketamine includes (R,S)-ketamine, (R)-ketamine and (S)-ketamine.

In certain embodiments, therapeutic agent for treating depression or anxiety is a muscarinic cholinergic antagonist. Non limiting examples of muscarinic cholinergic antagonist include benactyzine, benztropine, clozapine, cyproheptadine danitracen, scopolamine and a combination thereof.

In some embodiments, the therapeutic agent for treating anxiety or depression drug is water soluble. The sustained release profile of the pharmaceutical composition prolongs the half-life and circulating concentration of the anti-depression or anti-anxiety drug, hence, sustains the therapeutic effect and reduces the frequency of drug administration.

In one aspect, the sustained release profile of the pharmaceutical composition is due to a high drug encapsulation efficiency. The encapsulation efficiency of the pharmaceutical composition is at least 50%, 55%, 60%, 65%, 70%, 75% or 80%.

In another aspect, sustained release profile of the pharmaceutical composition is due to a higher drug to lipid molar ratio. In an exemplary embodiment, the molar ratio of the one or more anti-depression or anti-anxiety drugs to the one or more lipids is above or equal to about 0.15, alternatively from about 0.15 to 10, from about 0.15 to 5, from about 0.15 to 3, from about 0.15 to 2 or from about 0.15 to 1.

In yet another aspect, the half-life of the therapeutic agent for treating depression or anxiety is extended by at least 2-fold, at least 5-fold, at least 7.5-fold, at least 10-fold, or at least 20-fold compared to that of the free therapeutic agent for treating depression or anxiety.

The invention also provides methods of treating depression or anxiety, comprise the administration of an effective amount of the pharmaceutical composition described herein to a subject in need thereof, whereby the symptoms and/or signs of the depression or anxiety in the subject are reduced.

The pharmaceutical composition is formulated to be suitable for cutaneous injection, such as subcutaneous, subdermal, intradermal or intramuscular route. The pharmaceutical composition is also formulated to be administered as a transdermal patch.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, any existing medical conditions, and on the discretion of medical professionals.

In one aspect, the pharmaceutical compositions disclosed herein display a significant extended-release profile of a NMDA receptor antagonist. For example, the pharmaceutical composition of the present invention extended the half-life of ketamine to 16.3 hours in rats (as disclosed in Example 3) compared to the half-life of either free ketamine via intraperitoneal injection in rat (1.3 hours, see J Am Assoc Lab Anim Sci. 2013; 52(5):567-70) or Ketalar (an FDA approved Ketamine Hydrochloride Injection), where the half-life is 2.5 hours via intravenous injection or intramuscular injection in human (see New Drug Application submitted package, Par Sterile Products, Application No.: 016812). This invention is developed to reduce the dosing frequency to twice-daily to daily, once every two days, once every three days, once every five days, weekly, once every two weeks, once a month, once every two months, once every three months, once every four months, once every five months or once every six months.

In another aspect, the pharmaceutical compositions disclosed herein display a significant extended-release profile of a muscarinic cholinergic antagonist. For example, the pharmaceutical composition of the present invention extends the half-life of subcutaneous administered liposomal scopolamine to 28.63 hours in rats (as disclosed in Example 6) compared to the half-life of free scopolamine administered via intravenous or subcutaneous injection in rats (0.28 or 0.60 hours, as disclosed in Example 6). This invention is directed to reducing the dosing frequency of a therapeutic agent for depression or anxiety to twice-daily to daily, once every two days, once every three days, once every five days, weekly, once every two weeks, once a month, once every two months, once every three months, once every four months, once every five months or once every six months.

EXAMPLES

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated.

Example 1. Preparation of Liposomal Ketamine Formulation

Empty liposomes were prepared by a lipid film hydration-extrusion method. HSPC, cholesterol, and DSPE-PEG2000 (mole percent 59.5/39.6/0.9) were dissolved in chloroform and a thin lipid film was formed by removing the organic solvent under vacuum in a rotary evaporator. The dry lipid film was hydrated in 75 mM triethylammonium sucrose octasulfate (pH 6.0) at 60° C. for 30 min and liposomes were formed with triethylammonium sucrose octasulfate encapsulated in the aqueous core. After six freeze-thaw cycles between liquid nitrogen and water at 60° C., the empty liposomes were subsequently extruded ten times through polycarbonate filter membranes with a pore size of 0.2 µm. Unencapsulated triethylammonium sucrose octasulfate was removed by dialysis against a 9.4% sucrose solution.

A reaction mixture containing 3.75 mg/mL of ketamine hydrochloride (Tocris Bioscience), 25 mM of lipids of empty liposomes and 10 mM histidine buffer (pH 6.5) was incubated at 60° C. for 30 min, and then the unencapsulated ketamine hydrochloride was separated by a Sephadex™ G-50 Fine gel (GE Healthcare) or dialysis bag (Spectrum Labs) against a 9.4% sucrose solution to obtain the liposomal ketamine formulation. Encapsulated ketamine hydrochloride concentrations and the lipid concentrations of the liposomal ketamine formulation were measured using an ultraviolet/visible (UV/Vis) spectrophotometer to calculate the drug to lipid molar ratio (D/L) of the liposomal ketamine formulation.

The encapsulation efficiency was calculated by the drug to lipid molar ratio (D/L) of the ketamine hydrochloride encapsulated liposomes compared to the nominal D/L of reaction mixture, which was divided the initial added concentration of ketamine hydrochloride by the initial added concentration of lipid of empty liposome. The particle size distribution was measured by a dynamic light scattering instrument (Zetasizer Nano-ZS90, Malvern).

Using 75 mM triethylammonium sucrose octasulfate as a trapping agent, the liposomal ketamine formulation has a final D/L of 0.52 and an encapsulation efficiency of 95.0%.

Example 2. The Effect of Different Trapping Agents on Ketamine Loading

The liposome formulations were prepared according to Example 1, with the following trapping agents: (1) 75 mM of triethylammonium sucrose octasulfate, (2) 250 mM of ammonium sulfate and (3) 300 mM of ammonium sulfate. The particle size distribution was measured by a dynamic light scattering instrument (Zetasizer Nano-ZS90, Malvern). Table 1 shows the effect of different trapping agents on ketamine loading.

TABLE 1

The ketamine loading profile of different trapping agents

| Bilayer Membranes (mole percent) | Trapping Agent | Purified D/L (mole/mole) | Encapsulation Efficiency (%) | Average Particle Size (nm) |
|---|---|---|---|---|
| HSPC/cholesterol/DSPE-PEG2000 (59.5/39.6/0.9) | 1 | 0.52 | 95.0 | n.d. |
| HSPC/cholesterol/DSPE-PEG2000 (58.3/38.8/2.9) | 2 | 0.44 | 79.5 | n.d. |
| DMPC/cholesterol/DSPE-PEG2000 (59.5/40/0.5) | 3 | 0.22 | 60.4 | 191.5 | n.d., not determined.

Example 3. Pharmacokinetics (PK) Study of Liposomal Ketamine Formulation

An in vivo PK evaluation of the liposomal ketamine formulation was performed using 7- to 8-week-old female Sprague-Dawley rats. The rats were housed in a holding room which operated on a 12-hr light/12-hr dark circadian cycle with free access to water and food.

The rats were divided into two groups (n=3 in each group), one group received subcutaneous (SC) injection of 5.0 mg/kg of free ketamine hydrochloride, prepared by dissolving ketamine hydrochloride in 9.4% sucrose solution with a final concentration of 1.0 mg/mL. The other group received subcutaneous injection of 25 mg/kg of liposomal ketamine formulation, prepared according to Example 1. Blood samples were collected at 15 min, 0.5, 1, 2, 4, 6, 8, 24 and 48 hours post-injection. Plasma samples were obtained by centrifugation, kept frozen at −80° C. and analyzed using a noncompartmental analysis model in PKSolver (Comput Methods Programs Biomed. 2010; 99(3):306-314). The PK parameters of the two ketamine formulations are summarized in Table 2.

The results in Table 2 show the dose-normalized $C_{max}$ of liposomal ketamine was 34.5% of that of free ketamine, the half-life ($t_{1/2}$) of liposomal ketamine (16.3 h) was significantly longer compared to that of the free ketamine (0.77 h), and the dose-normalized area under the curve ($AUC_{0-t}$/dose and $AUC_{0-inf}$/dose) indicates that almost all the ketamine was released from liposomes, assuming that $AUC_{0-inf}$/dose of free ketamine is based on 100% drug released.

Compared to the published clinical date on intravenous (IV) infusion of free ketamine (SR Edwards et al., Br J Anaesth. 2002; 88(1):94-100), the $t_{1/2}$ of liposomal ketamine (16.3 h) was significantly longer compared to the intravenous (IV) infusion of free ketamine (0.63 h).

TABLE 2

PK parameters derived from rats after single subcutaneous injection of free ketamine and liposomal ketamine formulation

| Parameters | Free Ketamine SC | Liposomal Ketamine Formulation SC | Free Ketamine[†] IV |
|---|---|---|---|
| Dosage (mg/kg) | 5.0 | 25.0 | 50.0 |
| $t_{1/2}$ (h) | 0.77 | 16.3 | 0.63 |
| $C_{max}$ (ng/mL) | 190.0 | 328.7 | — |
| $C_{max}$/dose | 38.0 | 13.1 | — |
| $AUC_{0-t}$ (ng/mL * h) | 305.1 | 1940.9 | — |
| $AUC_{0-t}$/dose | 61.0 | 77.6 | — |
| $AUC_{0-inf}$ (ng/mL * h) | 314.4 | 2237.8 | — |
| $AUC_{0-inf}$/dose | 62.9 | 89.5 | — |

[†]Data extracted from Br J Anaesth. 2002; 88(1): 94-100 in Wistar rats after IV infusion of ketamine at 10 mg · kg$^{-1}$ · min$^{-1}$ over 5 min.

Figure 1:
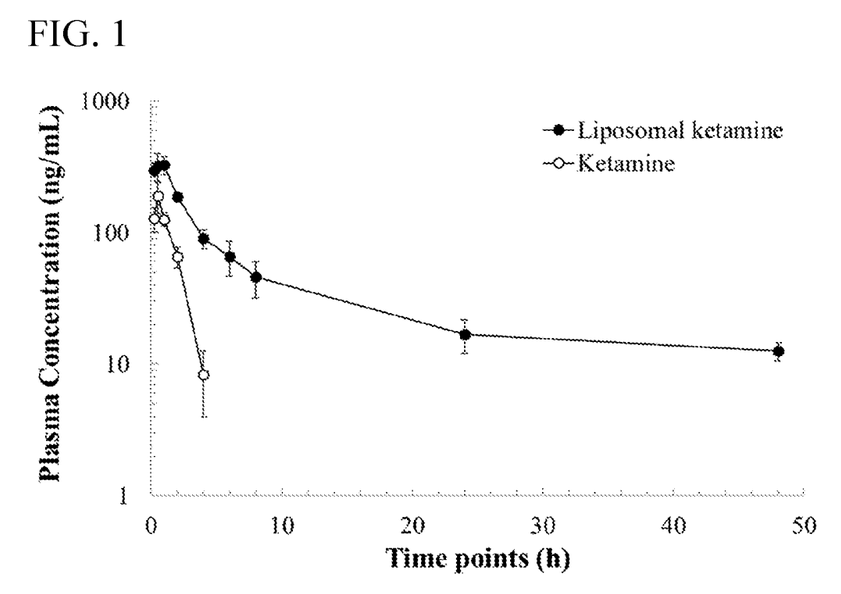
FIG. 1 is a line graph showing the plasma ketamine concentration in rats after subcutaneous injection of liposomal ketamine and free ketamine.
Figure 2:
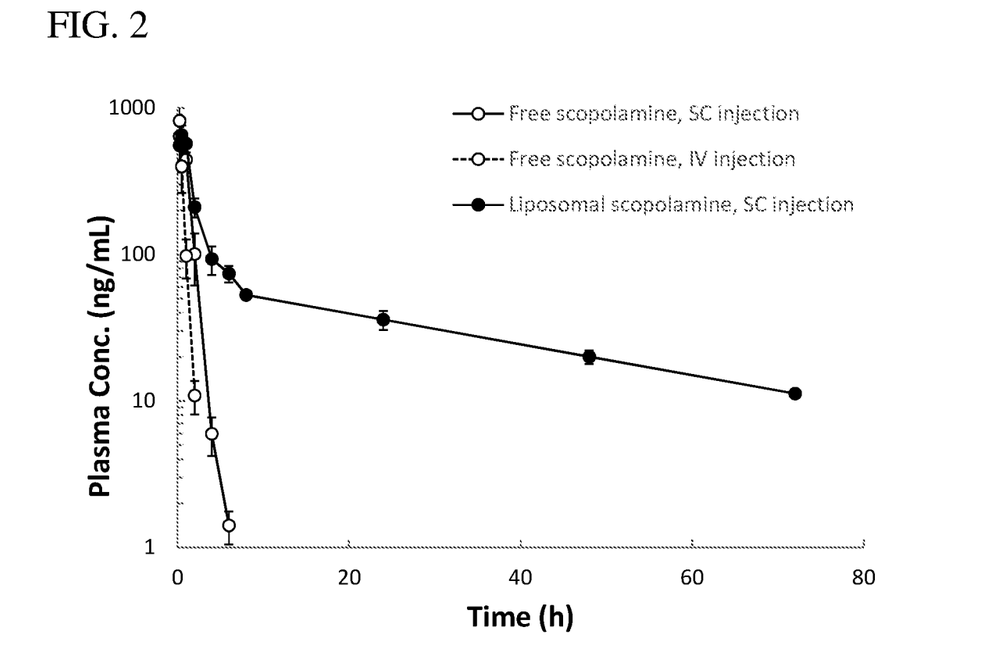
FIG. 2 is a line graph showing the plasma scopolamine concentration in rats after subcutaneous (SC) injection of liposomal scopolamine formulation and free scopolamine, and intravenous (IV) injection of free scopolamine.

In addition, FIG. 1 shows ketamine was undetectable in the plasma of rats receiving SC injection of free ketamine 4 hours post drug injection whereas ketamine was detected in the plasma of rats receiving SC injection of liposomal ketamine up to 48 hours post drug injection. The results support a conclusion that the claimed pharmaceutical composition sustained the release of ketamine.

Example 4. Preparation of Liposomal Scopolamine Formulation

Empty liposomes were prepared by a lipid film hydration-extrusion method or a solvent-injection method. For the lipid film hydration method, bilayer membrane components (e.g., HSPC/cholesterol/DSPE-PEG2000 at mole percent of 59.5/39.6/0.9) were dissolved in an organic solvent, for example, chloroform and dichloromethane. A thin lipid film was formed by removing the organic solvent under vacuum in a rotary evaporator. The dry lipid was hydrated in a trapping agent, for example, 300 mM ammonium sulfate, for 30 min at the temperature above the transition temperature of lipids to form the MLVs. Other trapping agents, such as ammonium phosphate or triethylammonium sucrose octasulfate, were also used. For the solvent injection method, bilayer membrane components (HSPC/cholesterol/DSPE-PEG2000 at mole percent of 59.5/39.6/0.9) were dissolved in an organic solvent and then injected into a stirring aqueous solution containing a trapping agent to form the MLVs. After extrusion through polycarbonate filter membranes with a pore size of 0.2 μm, unencapsulated trapping agent was removed by dialysis method or diafiltration method against 9.4% sucrose solution to create a polyatomic ion gradient between inner aqueous phase and outer aqueous phase of the empty liposomes.

A reaction mixture containing 4.0 mg/mL of scopolamine hydrobromide trihydrate (Sigma Aldrich, USA), empty liposomes with 40 mM of lipids prepared according to the preceding paragraph and 10 mM histidine buffer (pH 6.5) was incubated at 60° C. for 30 min. The unencapsulated scopolamine hydrobromide trihydrate was separated by a Sephadex™ G-50 Fine gel (GE Healthcare, USA) or a dialysis bag (Spectrum Labs, USA) against a 9.4% sucrose solution to obtain the liposomal scopolamine formulation.

Encapsulated scopolamine hydrobromide trihydrate concentration and the lipid concentration of the liposomal scopolamine formulation were measured using a HPLC and an ultraviolet/visible (UV/Vis) spectrophotometer to calculate the drug to lipid molar ratio (D/L) of the liposomal scopolamine formulation. The particle size distribution was measured by a dynamic light scattering instrument (Zetasizer Nano-ZS90, Malvern).

Using 300 mM ammonium sulfate as a trapping agent, the liposomal scopolamine formulation has a final D/L of 0.18, an encapsulation efficiency of 82.1% and the mean diameter of the liposomes was 195.0 nm.

Example 5. The Effect of Different Trapping Agents on Scopolamine Loading Profile The liposome formulations were prepared according to Example 4, with the following trapping agents: (1) 300 mM of ammonium sulfate, (2) 250 mM of ammonium sulfate, (3) 75 mM of triethylammonium sucrose octasulfate, and (4) 200 mM ammonium phosphate. Table 3 shows the effect of different trapping agents on the loading of scopolamine into the liposomal formulation.

TABLE 3

The scopolamine loading profile of different trapping agents

| Bilayer Membranes (mole percent) | Trapping Agent | Purified D/L (mole/mole) | Encapsulation Efficiency (%) | Average Particle Size (nm) |
|---|---|---|---|---|
| HSPC/cholesterol/DSPE-PEG2000 (59.5/39.6/0.9) | 1 | 0.18 | 80.6 | 195.0 |
| HSPC/cholesterol/DPPG (59.5/39.6/0.9) | 1 | 0.15 | 66.9 | 206.6 |
| HSPC/cholesterol/DSPE-PEG2000 (58.3/38.8/2.9) | 2 | 0.27 | 58.1 | n.d. |
| HSPC/cholesterol/DSPE-PEG2000 (59.5/39.6/0.9) | 3 | 0.37 | 81.1 | n.d. |
| HSPC/cholesterol (60/40) | 3 | 0.15 | 66.6 | 194.8 |
| HSPC/cholesterol/DSPE-PEG2000 (48/32/20) | 3 | 0.17 | 73.3 | 226.6 |
| DPPC/cholesterol/DSPE-PEG2000 (59.5/39.6/0.9) | 4 | 0.15 | 63.8 | 179.8 | n.d., not determined.

Example 6. Pharmacokinetics (PK) Study of Liposomal Scopolamine Formulation

An in vivo PK evaluation of the liposomal scopolamine formulation was performed using 7- to 8-week-old female Sprague-Dawley rats. The rats were housed in a holding room which operated on a 12-hr light/12-hr dark circadian cycle and had free access to water and food.

The rats were divided into three groups, the rats in the first group (n=3) each received a subcutaneous (SC) injection of 5.0 mg/kg of free scopolamine hydrobromide trihydrate, prepared by dissolving scopolamine hydrobromide trihydrate in 9.4% sucrose solution with a final concentration of 1.0 mg/mL; the rats in the second group (n=4) each received a subcutaneous injection of 25 mg/kg of liposomal scopolamine formulation prepared according to Example 4, using 75 mM of triethylammonium sucrose octasulfate as trapping agent; the rats in the third group (n=3) each received an intravenous (IV) injection of 2.0 mg/kg of free scopolamine hydrobromide trihydrate, prepared by dissolving scopolamine hydrobromide trihydrate in 9.4% sucrose solution with a final concentration of 2.0 mg/mL. Blood samples were collected at 15 and 30 min, 1, 2, 4, 6, 8, 24, 48 and 72 hours post-injection. Plasma samples were obtained by centrifugation, kept frozen at −80° C. and analyzed using liquid chromatography-tandem mass spectrometry. The plasma concentrations versus time curves were analyzed using a noncompartmental analysis model in PKSolver (Comput Methods Programs Biomed. 2010; 99(3):306-314). The PK parameters of the three study groups are summarized in Table 4.

The results in Table 4 show the dose-normalized $C_{max}$ ($C_{max}$/dose) of the liposomal scopolamine formulation was 20% of that of the free scopolamine administered by SC injection, the half-life ($t_{1/2}$) of the liposomal scopolamine formulation (28.63 h) was significantly longer compared to that of the free scopolamine administered by SC injection (0.60 h), and the dose-normalized area under the curve ($AUC_{0-inf}$/dose) indicates that 84% the scopolamine was released from liposomes, assuming that $AUC_{0-inf}$/dose of free scopolamine is based on 100% drug released. There was no initial burst release of scopolamine into the circulation in rats received SC liposomal scopolamine formulation injection due to the low $C_{max}$, which minimizes the toxicity or unwanted side effect and increases the injection dose window of liposomal scopolamine formulation in clinical use. These PK results demonstrate the extended release PK profile of the liposomal scopolamine formulation with reduced toxicity.

TABLE 4

PK parameters derived from rats after a single intravenous injection of free scopolamine, a single subcutaneous injection of liposomal scopolamine formulation or free scopolamine

| Parameter | Free Scopolamine IV | Free Scopolamine SC | Liposomal Scopolamine Formulation SC | Ratio (liposome/free) SC/SC |
|---|---|---|---|---|
| Dosage (mg/kg) | 2 | 5 | 25 | — |
| Sample size | 3 | 3 | 4 | — |
| $t_{1/2}$ (h) | 0.28 | 0.60 | 28.63 | 4772% |
| $C_{max}$ (ng/ml) | 814.00 | 639.67 | 651.50 | — |
| $C_{max}$/dose | 407.00 | 127.93 | 26.06 | 20% |
| $AUC_{0-t}$ (ng/mL * h) | 639.34 | 885.79 | 2363.51 | — |
| $AUC_{0-inf}$ (ng/mL * h) | 643.78 | 887.02 | 3726.10 | — |
| $AUC_{0-inf}$/dose | 321.89 | 177.40 | 149.04 | 84% |

In addition, FIG. 2 shows scopolamine was detected in the plasma of rats receiving SC injection of liposomal scopolamine formulation up to 72 hours post drug injection, whereas scopolamine was undetectable within 2 hours of IV administration or within 6 hours of SC administration of free scopolamine. The results support a conclusion that the claimed pharmaceutical composition sustained the release of scopolamine.

The invention claimed is:

1. A pharmaceutical composition, comprising (a) at least one liposome comprising a bilayer membrane, said bilayer membrane comprises a first lipid that is HSPC, DMPC or any combination thereof, cholesterol and a second lipid that is PEG-DSPE;

(b) a trapping agent that is triethylammonium sucrose octasulfate, ammonium sulfate, or any combination thereof; and (c) a therapeutic agent that is ketamine, wherein the molar ratio of the therapeutic agent to the lipid is equal to or higher than about 0.2, the therapeutic agent is encapsulated in the liposomes with an encapsulation efficiency higher than about 60% and the mean particle size of the liposome is from about 50 nm to about 20 μm.

2. The pharmaceutical composition of claim 1, wherein the mole % of first lipid: second lipid: cholesterol is 40-70%: 0.1-25%: 25-45%.

3. The pharmaceutical composition of claim 1, wherein the concentration of triethylammonium sucrose octasulfate is about 10 to 200 mM.

4. The pharmaceutical composition of claim 1, wherein the concentration of ammonium sulfate is about 100 to 600 mM.

5. The pharmaceutical composition of claim 1, wherein the bilayer membrane comprises a first lipid that is HSPC, cholesterol and a second lipid that is PEG-DSPE, with an encapsulation efficiency higher than about 75%.

6. The pharmaceutical composition of claim 1, wherein said ketamine is selected from the group consisting essentially of (R,S)-ketamine, (R)-ketamine and (S)-ketamine.

7. The pharmaceutical composition of claim 1, further comprising a pharmaceutically acceptable excipient, a diluent, a medium for an active ingredient, a preservative, a cryoprotectant or a combination thereof.

8. A method of treating depression or anxiety, comprising: administering the pharmaceutical composition of claim 1 to a subject in need thereof.

9. The method of claim 8, wherein the half-life of the therapeutic agent in the pharmaceutical composition is extended by at least 2-fold compared to that of a free therapeutic agent.

10. The method of claim 8, wherein the pharmaceutical composition is administered at least once every three days, at least once every week, at least once every two weeks or at least once a month.

11. The method of claim 8, wherein the pharmaceutical composition is administered by cutaneous injection.

12. The method of claim 11, wherein the cutaneous injection includes subcutaneous, subdermal, intradermal or intramuscular route.

13. A pharmaceutical composition, comprising
    (a) at least one liposome comprising a bilayer membrane, said bilayer membrane comprises a first lipid that is HSPC, DPPC or any combination thereof, cholesterol and optionally a second lipid that is PEG-DSPE, DPPG or any combination thereof;
    (b) a trapping agent that is 10 to 200 mM triethylammonium sucrose octasulfate, 300 to 600 mM ammonium sulfate, 100 to 600 mM ammonium phosphate or any combination thereof; and
    (c) a therapeutic agent that is scopolamine,
wherein the molar ratio of the therapeutic agent to the lipid is equal to or higher than about 0.15, the therapeutic agent is encapsulated in the liposomes with an encapsulation efficiency higher than about 60% and the mean particle size of the liposome is from about 50 nm to about 20 μm.

14. The pharmaceutical composition of claim 13, wherein the mole % of first lipid: second lipid: cholesterol is 40-70%: 0.1-25%: 25-45%.

15. The pharmaceutical composition of claim 13, wherein the trapping agent is 10 to 200 mM triethylammonium sucrose octasulfate, 300 to 600 mM ammonium sulfate, or any combination thereof; the molar ratio of the therapeutic agent to the lipid is equal to or higher than about 0.15, the therapeutic agent is encapsulated in the liposomes with an encapsulation efficiency higher than about 65%.

16. The pharmaceutical composition of claim 13, further comprising a pharmaceutically acceptable excipient, a diluent, a medium for an active ingredient, a preservative, a cryoprotectant or a combination thereof.

17. A method of treating depression or anxiety, comprising:
administering the pharmaceutical composition of claim 13 to a subject in need thereof.

18. The method of claim 17, wherein the half-life of the therapeutic agent in the pharmaceutical composition is extended by at least 2-fold compared to that of a free therapeutic agent.

19. The method of claim 17, wherein the pharmaceutical composition is administered at least once every three days, at least once every week, at least once every two weeks or at least once a month.

20. The method of claim 17, wherein the pharmaceutical composition is administered by cutaneous injection.

\* \* \* \* \*